United States Patent
Ishiwatari

[11] Patent Number: 5,925,371
[45] Date of Patent: Jul. 20, 1999

[54] ARTHROPOD REPELLENT AND METHOD FOR REPELLING ARTHROPODS

[75] Inventor: Takao Ishiwatari, Osaka, Japan

[73] Assignee: Sumitomo Chemical Co., Ltd., Osaka, Japan

[21] Appl. No.: 08/993,521

[22] Filed: Dec. 18, 1997

[30] Foreign Application Priority Data

Dec. 18, 1996 [JP] Japan .................................. 8-338669

[51] Int. Cl.$^6$ .......................... A01N 25/10; A01N 25/18; A01N 31/06
[52] U.S. Cl. .................. 424/414; 424/405; 424/DIG. 10
[58] Field of Search ............................ 424/405, DIG. 10, 424/409, 411, 414; 568/875

[56] References Cited

U.S. PATENT DOCUMENTS 5,130,136  7/1992  Shono et al. ........................... 424/405
5,608,088  3/1997  Watanabe et al. ...................... 549/529
5,698,209  12/1997  Shono et al. .......................... 424/405

FOREIGN PATENT DOCUMENTS

476885 A2  3/1992  European Pat. Off. .
792581 A1  9/1997  European Pat. Off. .

*Primary Examiner*—Robert H. Harrison
*Attorney, Agent, or Firm*—Pillsbury Madison & Sutro LLP

[57] ABSTRACT

The present invention provides an arthropod repellent comprising a cellulose material having a bulk density of 0.2 to 0.7 g/cm$^3$ containing carane-3,4-diol as an active ingredient, said cellulose material having the composition supported thereon or being impregnated with the composition. The cellulose material has generally thickness of 3 to 8 mm. The arthropod repellent of the present invention is used under heating condition and shows the lasting efficacy of repellency.

6 Claims, No Drawings

ARTHROPOD REPELLENT AND METHOD FOR REPELLING ARTHROPODS

TECHNICAL FIELD

The present invention relates to an arthropod repellent and a method for repelling arthropods.

BACKGROUND ART

It is known, as described in U.S. Pat. No. 5,130,136, that carane-3,4-diol is effective in repelling noxious arthropods, especially blood-sucking insects such as mosquito and the like.

In the meantime, a noxious arthropod repellent is, in general, applied directly to the skin or an exposed portion of the skin is covered with a base material treated with a noxious arthropod repellent, and the usage of a noxious arthropod repellent by means of a vaporization under heating condition, as observed in the case of an insecticidal tablet or mat used on electric heater, is not conducted. In fact, active ingredients of known arthropod repellents have generally a high volatility in its nature and a problem is expected that volatilization occurs within quite a short period of time when an arthropod repellent is applied for use by means of a vaporization under heating condition. Therefore, the usage of an arthropod repellent by means of a vaporization under heating condition was completely out of the question.

DISCLOSURE OF THE INVENTION

The object of the present invention is to provide a method for repelling arthropods by means of a vaporization under heating condition and to provide an arthropod repellent suitable for the method mentioned above.

In the present invention, carane-3,4-diol was chosen as the active ingredient, and as a result that the active ingredient mentioned above is supported in a cellulose material having the bulk density within the range of 0.2 to 0.7 g/cm$^3$, the present invention enables to provide a noxious arthropod repellent applicable for use by means of a vaporization under heating condition and to provide a method for repelling noxious arthropods by heating the arthropod repellent mentioned above.

Carane-3,4-diol has various stereoisomers, and in the present invention one of the active isomers or mixture thereof is used. Particularly, it is preferable to use 1S, 3S, 4S, 6R-carane-3,4-diol or 1S, 3R, 4R, 6R-carane-3,4-diol, or the mixture of carane-3,4-diol isomers containing the high ratio of 1S, 3S, 4S, 6R-carane-3,4-diol and/or 1S, 3R, 4R, 6R-carane-3,4-diol, as these have a high activity of repellency.

A cellulose material used in the present invention has a bulk density within the range of 0.2 to 0.7 g/cm$^3$, and practically the paper having the bulk density such as pulp and cotton linters and the like is used. The thickness of the cellulose material mentioned above is not particularly restricted. However, when the material has the thickness within the range of 3 to 8 mm, the heating apparatus for insecticidal tablet or mat used on electric heater which is in common use can be utilized without any modifications to heat the material up to 130 to 170° C.

An arthropod repellent in the present invention is manufactured as follows; carane-3,4-diol is dissolved, if necessary, into the appropriate solvent such as acetone, ethanol and isopropyl alcohol and the like, and then the solution is soaked in a cellulose material. Generally, carane-3,4-diol is retained in a cellulose material with the amount of 10 to 1,000 mg/cm$^2$.

An arthropod repellent in the present invention is generally prepared with the size of ca. 2.2 cm×3.5 cm and is put on the heating portion of the heating apparatus for common insecticidal tablet or mat to be heated up to the temperature of 130 to 170° C. The arthropods to be repelled by this method include various kinds of noxious Arthropod, that is, mosquitoes represented by Aedes spp. such as *Aedes aegypti* and *Aedes albopictus*, Anopheles spp. such as *Anopheles albimanus* and Culex spp. such as Culex pipiens pallens (common mosquito) and *Culex tritaeniorhynchus*, bloodsucking insects such as gnats, stable flies, sand flies, biting midges and fleas, unpleasant and insanitary insects such as Muscidae (*Musca domestica* (housefly), *Muscina stabulans* (false stablefly), *Fannia canicularis* (little housefly), etc.), Psychodidae and Phoridae, and ticks.

EXAMPLES

The present invention is illustrated by the following preparation examples and test example.

Preparation Example 1

Acetone solution (1 ml) containing 40% (w/v) 1S,3S,4S, 6R-carane-3,4-diol was dropped on a cellulose paper having the thickness of 4.0 mm and the bulk density of 0.45 g/cm$^3$ so that the solution was soaked into the paper. Then the paper was dried by air and an arthropod repellent in the present invention was obtained.

Preparation Example 2

Acetone solution (1 ml) containing 40% (w/v) 1S,3S,4S, 6R-carane-3,4-diol was dropped on a cellulose paper having the thickness of 6.2 mm and the bulk density of 0.39 g/cm$^3$ so that the solution was soaked into the paper. Then the paper was dried by air and an arthropod repellent in the present invention was obtained.

The following reference examples are the preparation examples of an arthropod repellent to be employed for the comparison in the test example illustrated below.

Reference Example 1

Acetone solution (1 ml) of containing 40% (w/v) 1S,3S, 4S,6R-carane-3,4-diol was dropped on a cellulose paper having the thickness of 0.32 mm and the bulk density of 0.73 g/cm$^3$ so that the solution was soaked into the paper. Then the paper was dried by air and an arthropod repellent to be employed for the comparison was obtained.

Reference Example 2

Acetone solution (1 ml) containing 40% (w/v) 1S,3S,4S, 6R-carane-3,4-diol was dropped on a cellulose paper having the thickness of 0.40 mm and the bulk density of 0.17 g/cm$^3$ so that the solution was soaked into the paper. Then the paper was dried by air and an arthropod repellent to be employed for the comparison was obtained.

Test Example 1

Approximately 200 males and 200 females of *Aedes aegypti* were kept in a cage made of nylon gauze having the size of 30 cm×20 cm×20 cm, and a disposable body warmer (a small package of plastic film including iron powder and catalyst accelerating oxygenation) was installed on the ceiling of the cage as an attractant. (Every disposable body warmer was unsealed approximately 10 minutes before served for each examination.) The arthropod repellents of Preparation Example 1 and 2, and Reference Example 1 and 2 were put on the electric heating apparatus having the surface temperature of 160° C. After the electric heating apparatus was electrified for a certain period of time (see Table 1), each arthropod repellent was installed beneath the disposable body warmer inside the cage. The number of *Aedes aegypti* attracted by the disposable body warmer was counted 1 minute after the initiation of the examination, and the ratio of repellency was calculated according to the following formula The ratio of repellency (%) =

$$\frac{\text{attracted number to body warmer (non-treated)} - \text{attracted number to body warmer (repellent-treated)}}{\text{attracted number to body warmer (non-treated)}} \times 100$$

For the body warmer in non-treated area in the above formula, the same cellulose paper as that employed in Preparation Example 1 without containing the active ingredient was heated on the heating apparatus at the temperature of 160° C. The result is shown in Table 1. In Table 1, ○ stands for more than 90% of the ratio of repellency, Δ stands for more than 50% and less than 90% of the ratio of repellency, and x stands for less than 50% of the ratio of repellency.

TABLE 1

| | Duration after the heating apparatus was electrified | | |
|---|---|---|---|
| | 1 hour | 4 hours | 8 hours |
| Preparation Example 1 | ○ | ○ | ○ |
| Preparation Example 2 | ○ | ○ | ○ |
| Reference Example 1 | ○ | ○ | X |
| Reference Example 2 | ○ | Δ | X |

An arthropod repellent in the present invention is suitable for use under heating condition and shows the lasting efficacy of repellency for a long time.

What is claimed is:

1. An arthropod repellent comprising
   cellulose paper having a bulk density of 0.2 to 0.7 g/cm$^3$; and
   an active ingredient comprising carane-3,4-diol,
   wherein said cellulose paper is impregnated with said active ingredient or the active ingredient is supported on said cellulose paper.

2. An arthropod repellent according to claim 1, wherein the cellulose material has a thickness of 3 to 8 mm.

3. The arthropod repellent according to claim 1, wherein said active ingredient comprises 1S, 3S, 4S, 6R-carane-3,4-diol.

4. The arthropod repellent according to claim 1, wherein said active ingredient comprises 1S, 3R, 4R, 6R-carane-3,4-diol.

5. A method for repelling arthropods comprising:
   heating an arthropod repellent according to claim 1 or 2.

6. A method for repelling arthropods according to claim 5, wherein the heating to a temperature within the range of 130° C. to 1 70° C.

* * * * *